United States Patent [19]
Giese et al.

[11] Patent Number: 5,412,083
[45] Date of Patent: May 2, 1995

[54] CARBOHYDRATE HETEROBIFUNCTIONAL CROSS-LINKING REAGENT

[75] Inventors: Roger W. Giese, Quincy, Mass.; Kailin Guan, Lawrenceville, N.J.; Douglas J. Cecchini, Jamaica Plain, Mass.

[73] Assignee: Northeastern University, Boston, Mass.

[21] Appl. No.: 871,221

[22] Filed: Apr. 16, 1992

[51] Int. Cl.$^6$ ............... C07H 5/04; C07H 5/06; C08B 37/08
[52] U.S. Cl. .................................. 536/20; 536/55.2
[58] Field of Search ............... 536/20, 55.2, 18.7; 514/55

[56] References Cited

PUBLICATIONS

Davies et al, "[52] Determination of the Degree of Acetylation of Chitin and Chitosan", Methods in Enzymology 161:442–446 (1988).
Hirano, "[45] Water–Soluble Glycol Chitin and Carboxymethylchitin", Methods in Enzymology 161:408–410 (1988).
Muzzarelli, "Chitin", Pergamon Press, pp. 119–120 (1977).
Ohtakara, "[49] Viscosimetric Assay for Chitinase", Methods in Enzymology 161:426–430 (1988).
Pietersz, "The Linkage of Cytotoxic Drugs to Monoclonal Antibodies for the Treatment of Cancer", Bioconjugate Chemistry 1(2):89–95 (1990).
Wong, "Chemistry of Protein Conjugation and Cross–Linking", CRC Press, Inc. Table of Contents and p. 153.
Yamada et al, "A convenient synthesis of glycolchitin, a substrate of lysozyme" Carbohydrate Research 92:160–162 (1981).
Chemical Abstracts, vol. 104, No. 19, issued 12 May 1986, Hirano et al, "Preparation of Acetylated Derivatives of Modified Chito-oligosaccharides by the Depolymerization of Partially N-acetylated Chitosan with Nitrous Acid" see p. 698, col. 2, Abstract No. 168720z, Carbohydr. Res. 1985, 144(2), 338–41 (Eng).

Primary Examiner—Douglas W. Robinson
Assistant Examiner—Everett White
Attorney, Agent, or Firm—Weingarten, Schurgin, Gagnebin & Hayes

[57] ABSTRACT

A heterobifunctional cross-linking reagent having a carbohydrate backbone (derived from a chitin substrate) is disclosed. The cross-linker is available in a variety of lengths, is highly water-soluble, and can be formulated to undergo cleavage catalyzed by the enzyme lysozyme.

17 Claims, 1 Drawing Sheet

FIG. 1

CARBOHYDRATE HETEROBIFUNCTIONAL CROSS-LINKING REAGENT

FIELD OF THE INVENTION

The invention relates to cross-linking reagents containing two different types of compatible reactive functional groups.

BACKGROUND OF THE INVENTION

A heterobifunctional cross-linking reagent is a molecular substance containing two different types of reactive functional groups that are compatible, i.e., the groups chosen do not cross-react, so that a cross-linking reagent containing them is a relatively stable molecule. Such a reagent can be represented by the designation $F_1$-B-$F_2$ where $F_1$ represents one or more of a first functional group, $F_2$ similarly represents one or more of a second functional group that is different from $F_1$, and B is the backbone of the molecule.

The basic purpose of a $F_1$-B-$F_2$ reagent is to form a covalent linkage between two different molecular components. If the two molecular components are on the same substrate molecule, then an intramolecular cross-link is achieved. If the two molecular components are on different substrate molecules, then the cross-linking is intermolecular, i.e., the two substrate molecules (e.g., $S_1$ and $S_2$) are covalently joined together by the cross-linking reagent, forming "$S_1$-$F_1$-B-$F_2$-$S_2$," which can be abbreviated "$S_1$-$S_2$."

For both intramolecular and intermolecular cross-linking, two types of $F_1$-B-$F_2$ reagents can be considered. The first is a cleavable $F_1$-B-$F_2$, in which the linkage formed by $F_1$-B-$F_2$ on a substrate molecule, or between two substrate molecules, can be reversed under relatively mild, specific conditions. Such conditions, by definition, essentially preserve the structure and/or function of the substrate molecule(s). The second kind of $F_1$-B-$F_2$ reagent forms a noncleavable linkage with respect to subsequent exposure of the linkage to mild, specific conditions.

Both cleavable and noncleavable $F_1$-B-$F_2$ are useful, depending on the application. For example, an "antibody-$F_1$-B-$F_2$-enzyme" reagent may be formed for use in an immunoassay. If it is important to keep the enzyme attached to the antibody throughout the assay, then a noncleavable $F_1$-B-$F_2$ reagent would be selected. For immunotherapy, an "antibody-$F_1$-B-$F_2$-toxin" therapeutic agent may be formed in which it is desirable for the toxin to be released at some point from the antibody. In this case, a cleavable $F_1$-B-$F_2$ reagent would be selected.

The general usefulness of an $F_1$-B-$F_2$ reagent is to serve as a molecular tool to combine the properties of substrate molecules. Largely, the applications are biomedical (e.g., diagnostic or therapeutic) or environmental, in which biological molecules like proteins and nucleic acids are at least one of the substrates. Other common substrates, especially for intermolecular cross-linking to one of these two species, are drugs, radionuclides, lipids, carbohydrates, enzyme inhibitors, haptens, signal groups (e.g., fluorophores), metal-chelating groups, and toxins. Also, $F_1$-B-$F_2$ reagents are used to immobilize these kinds of molecules to a solid support such as a chromatographic particle or to the well of a microtiter plate. The resulting, insolubilized substrate then might be used for such applications as affinity chromatography or ligand assay.

$F_1$-B-$F_2$ reagents are part of a larger class of cross-linking reagents that include homobifunctional and zero-length cross-linkers. The homobifunctional reagents possess only a single type of reactive functional group, and the zero-length reagents directly join two existing, functional groups on the substrate molecule(s) without becoming part of the link that develops. The latter are also more conventionally called "activating agents."

The advantage of the $F_1$-B-$F_2$ cross-linkers relative to the homobifunctional and zero-length cross-linkers is the greater control that the $F_1$-B-$F_2$ reagents can provide over the outcome of an intermolecular cross-linking event. Cross-linking with homobifunctional and zero-length cross-linkers tends to be random and produce undesirable side products. For example, the desired coupling of substrate $S_1$ to $S_2$ with a homobifunctional or zero-length cross-linker will often lead to the formation of $S_1$-$S_1$ and $S_2$-$S_2$ undesired products in addition to the desired $S_1$-$S_2$ product. Also, $S_1$, $S_2$ and $S_1/S_2$ polymers can form. Use of $F_1$-B-$F_2$ allows one to form just the $S_1$-$S_2$ product by establishing the specificity of $F_1$ for $S_1$ and the specificity of $F_2$ for $S_2$.

Carbohydrates have seen some use as homobifunctional cross-linking reagents. For example, drugs have been conjugated to dextran containing aldehyde, hydrazide, or amino groups (Pietersz, G. A., Bioconjugate Chem. 1:89-95 (1990); Wong, S. S., "Chemistry of Protein Conjugation and Cross-Linking," CRC Press, Boca Raton, (1991)).

SUMMARY OF THE INVENTION

In one aspect, the invention features a carbohydrate cross-linking reagent including a sequence of substituted glucosamine units in β-1,4 linkage. The reagent has a tetrahydrofuran unit at the reducing end and the general formula wherein each of $R_1$ or $R_2$ is H, $(CH_2CH_2O)_mH$, $(CH_2CH[CH_3]O)_mH$, $CH_2CO_2$ or $CH_2CH_2CN$, with m being an integer in the range of 1-10; wherein n is greater than or equal to 2; wherein $R_3$ and $R_4$ are acylating, alkylating, electrophilic or nucleophilic reactive groups which are different from each other but mutually compatible, and at least one $R_4$ is present; and wherein $R_5$ is an acyl group.

In another aspect of the invention, the substituent group $R_4$ is primarily or exclusively attached to the $C_4$ oxygen atom at the non-reducing end of the cross-linking reagent instead of just along the backbone of the molecule on one of the $C_2$ nitrogen atoms. This cross-linking reagent has the general formula wherein $R_1$, $R_2$, $R_3$, $R_4$ and $R_5$ are defined as above and n is greater than or equal to one.

Cross-linking reagents having a carbohydrate backbone are especially useful when formulated as heterobifunctional reagents, designated as $F_1$-B-$F_2$, since carbohydrates are available in a variety of lengths and are highly water-soluble. The shorter lengths can be used to minimize the distance between two substrate molecules that become connected to form a conjugate by the carbohydrate cross-linker. This may make it easier for the conjugate to be taken up by cells. It may help to control the relative orientation of the two substrate molecules to optimize their functional properties such as enzymatic activity or fluorescent energy transfer. It may help the conjugate to be more stable, more easily purified, less subject to adsorption losses, or more soluble.

For other substrate molecules to be cross-linked, the longer lengths for the carbohydrate cross-linker may be better suited to achieve some of these same properties. Often this is empirical and it is important to have reagents available with a variety of lengths so that several conjugates of the substrate molecules can be prepared for testing, and the best one selected for the most important properties. Preferably, the number of sugar residues in the linker is greater than or equal to ten, and more preferably, in the range of 10 to 100.

Certain properties, however, will benefit most by selecting a longer carbohydrate cross-linker. The first is the opportunity to establish a linkage between the substrate molecules that can be reversed under mild, specific conditions, especially by enzymatic catalysis. Only a longer carbohydrate cross-linker can be cleaved in this way because of steric effects. A longer chitin cross-linker is especially attractive for this purpose since lysozyme, the enzyme that catalyzes its cleavage, is small, stable and inexpensive. Further, the specificity of this enzyme means that it can be used to release an enormous variety of substrate molecules connected to each other or to a solid surface without disturbing the function of these substrate molecules. Further, lysozyme occurs in cells and in body fluids, making it attractive to use a chitin cross-linker to help deliver drugs to specific sites in the body and provide for the release of free drug at those sites.

Another important general application of a longer, enzyme cleavable carbohydrate cross-linker is in affinity chromatography or ligand assays in which a substrate molecule needs to be released from a solid surface for purification or detection purposes. Short cross-linkers between a solid surface and a substrate may cleave slowly or not at all due to steric effects, especially when the substrate is large, that is connected to the solid surface by the short cross-linker. A long carbohydrate cross-linker not only can overcome these problems, but take advantage of the very unique specificity of enzyme-catalyzed cleavage. Enzymes tend to be large molecules so that a long cross-linker is essential to enable the enzyme to achieve access to the cross-linker that connects the substrate to the solid surface.

The high water-solubility of carbohydrate cross-linkers can be useful by helping to maintain the water solubility of biological substrate molecules after they are cross-linked together or to other types of molecules. This property can also be helpful when a substrate molecule is attached by the carbohydrate cross-linker to a solid surface in an aqueous medium. In this case the cross-linker can help to project the substrate off the surface into the aqueous phase, where the substrate will be more accessible and thereby more readily can provide its function such as ligand binding or enzymatic activity towards other, dissolved molecules in the bulk aqueous phase.

The use of a chitin cross-linker with multiple functional groups along its side, and/or the repetitive use of such a cross-linker, can allow multiple copies of one substrate to be attached to another, thereby amplifying the function of one substrate relative to another in the conjugate. This can then intensify the detectability, catalytic throughput, or therapeutic power of the conjugate.

DESCRIPTION OF THE PREFERRED EMBODIMENTS

Chitin is a naturally occurring polysaccharide consisting of predominately N-acetylglucosamine residues. Glucosamine residues are typically present as well, and the polymer is called chitosan when the fraction of gluocosamines is significantly increased, as by deacetylating chitin with aqueous sodium hydroxide. While high molecular weight chitin is insoluble in water, related products such as glycolchitin and carboxymethylchitin can be prepared that are water soluble (Hirano, S., Meth. Enz. 161:408–410 (1988)).

Figure 1:
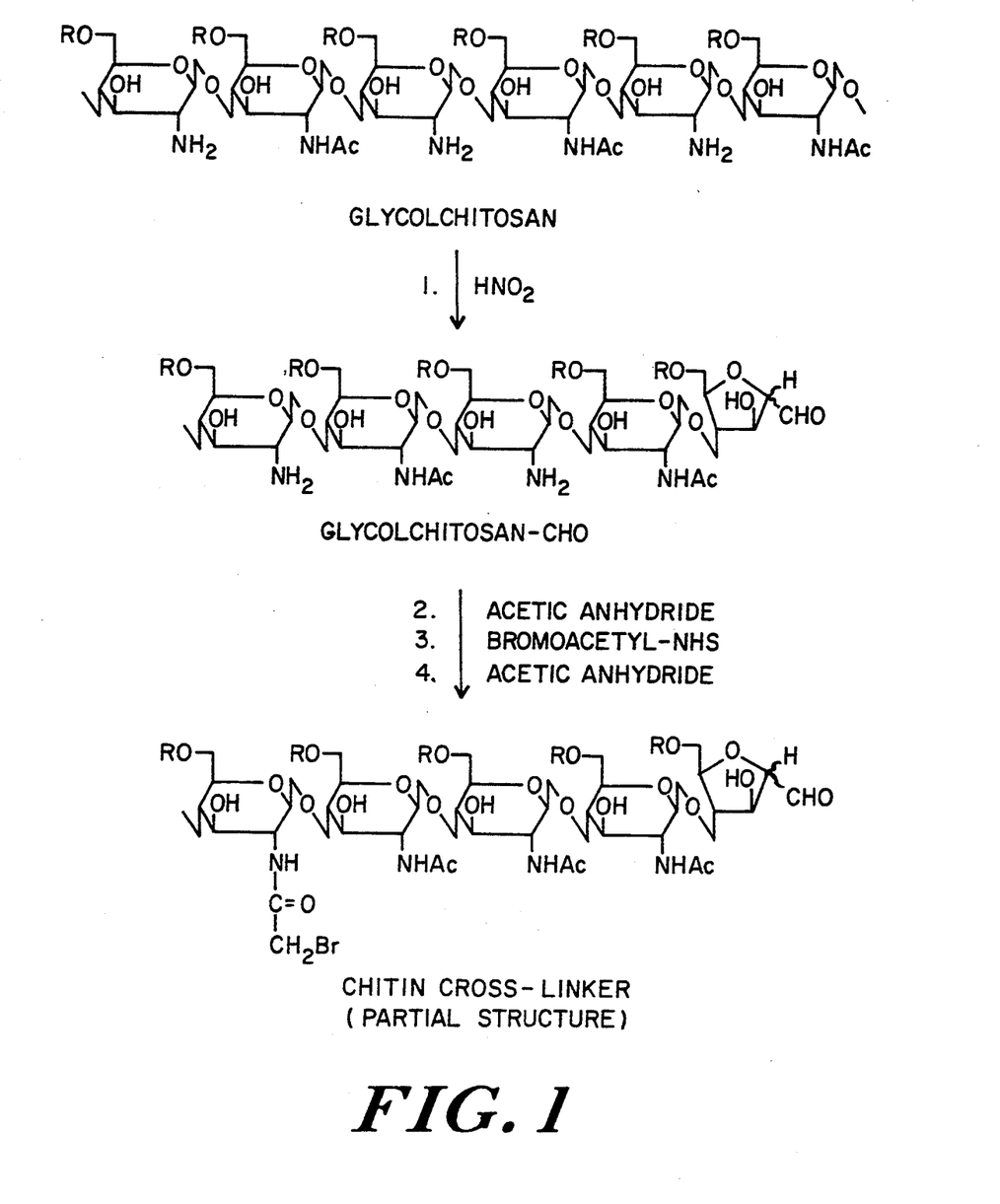
The FIGURE shows a method for the preparation of a chitin cross-linking reagent of the invention.

If glycolchitosan is properly oxidatively cleaved, acetylated, and reacted with a bromoacetyl transfer reagent under controlled conditions, a stable heterobifunctional cross-linker of about 40 sugar residues can be produced having an aldehyde at one end attached to a tetrahydrofuran ring and an average value of 2.6 bromoacetyl groups at presumably random positions along its length. Referring to FIG. 1, a chitin cross-linker is prepared by reacting glycolchitosan (where R=H or $(CH_2CH_2O)_mH$ where m is in the range of 1 to 10) with a limiting amount of nitrous acid to cleave oxidatively at just a limited number of the glucosamine linkage sites in the sugar backbone giving the intermediate product "glycolchitosan-CHO." This latter product is partly acetylated with acetic anhydride and reacted with bromoacetyl-N-hydroxy-succinimide (bromoacetyl-NHS). Since the cleavage products contain both residual amino groups and a terminal aldehyde, which potentially can react with each other, the reaction is immediately quenched with excess acetic anhydride, to acetylate any residual amino groups. The resulting chitin cross-linker is purified by size exclusion chromatography. For a starting molar ratio of nitrous acid to sugar residue of 0.125, the linker product had an average molecular weight of 10 kD, based on calibration of the chromatography column with dextran standards, corresponding to a length of about 40 sugar residues. Amounts of the acetic anhydride and bromoacetyl-NHS reagents were used that resulted in the cross-linker product being 80% active as a substrate for lysozyme, and possessing 2.6 bromoacetyl groups per molecule (as an average number). The measured number of aldehyde groups per chitin cross-linker was 0.9.

Other forms of the chitin cross-linker can be prepared by varying the length of the backbone portion and selecting other substituents. The length of the linker chain can be changed by varying the conditions of the oxidative-cleavage reaction, and/or by collecting different fractions when the resulting product mixture is purified by size exclusion chromatography. For example, shorter chitin cross-linkers can be obtained by increasing the amount of nitrous acid or the reaction time.

Forms of chitin or chitosan other than glycolchitosan can be used as substrates for cross-linker preparation. Some examples include carboxymethylchitosan (Hirano, S., Meth. Enz., 161:408–410 (1988)), hydroxypropylchitosan (Ohtakaro, A., Meth. Enz., 161:426–430 (1988)), cyanoethylchitosan (Muzzarelli, R. A. A., "Chitin," Pergamon Press, Oxford, p. 119–120 (1977)), and related chitosan derivatives.

The free amino groups on the selected chitosan derivative can be reacted with other reagents besides acetic anhydride and bromoacetyl-NHS. The use of acetic anhydride has a special purpose since the presence of N-acetylglucosamine residues on the chitosan chain makes it susceptible to enzyme-catalyzed cleavage by lysozyme. (Chitin, as a highly or fully N-acetylated derivative of chitosan, is a natural substrate for lysozyme.) Thus, chitin cross-linkers can be formed that range from very cleavable to noncleavable, depending on the degree of N-acetylation.

Two kinds of N-acetyl substituents can be covalently attached to the free amino groups of chitosan: inert and functional. Inert substituents would be acyl groups like acetyl, propionyl or benzoyl that would not have further reactivity properties on the chitin cross-linker with respect to its usage as a reagent. Functional substituents would possess a reactive, functional group that could be used, in turn, to attach the chitin cross-linker to another substance. Such functional groups can be acylating, alkylating, electrophilic or nucleophilic.

Examples of functional groups having an acylating functionality are a carbodiimide-activated carboxyl, an N-hydroxysuccinimide ester, a 1-hydroxybenzotriazole ester, an acyl azide, a nitrophenyl ester, an acyl imidazole, a cyanate ester, or a related group.

Functional groups having an alkylating functionality include an α-haloketo group, a maleimide, an epoxide, or a related group.

A functional group having an electrophilic functionality could be a nitrene precursor phenyl azide, an aldehyde, an aldehyde precursor oxidizable glycol, a disulfide, an α-diketone, a β-diketone, or a related group.

Functional groups having a nucleophilic functionality include a hydrazine, a hydrazide, a thiol, an amine, an oxyamine, or a related group.

Structures of these reactive functional groups are shown in Table I.

TABLE I

Structural Formulae for Functional Groups

| Description | Structure |
|---|---|
| carbodiimide-activated carboxyl | —C(=O)—O-carbodiimide[1] |
| N-hydroxysuccinimide ester | —C(=O)—O—N(succinimide) |
| 1-hydroxybenzotriazole ester | —C(=O)—O—N(benzotriazole) |
| nitrophenyl ester | —C(=O)—O—C$_6$H$_4$—NO$_2$ |
| acyl azide | —C(=O)—N$_3$ |
| acyl imidazole | —C(=O)—N(imidazole) |
| α-haloketo | —C(=O)—CH$_2$X (X = Cl, Br, I) |
| epoxide | —CH—CH$_2$ (epoxide) |
| maleimide | —N(maleimide) |
| nitrene precursor phenyl azide | C$_6$H$_4$—N$_3$ |
| cyanate ester | —O—C≡N |
| aldehyde | —C(=O)H |
| disulfide | —S—S—(pyridyl) |

TABLE I-continued
Structural Formulae for Functional Groups

| Description | Structure |
|---|---|
| α-diketone | $-\overset{\overset{O}{\|\|}}{C}-\overset{\overset{O}{\|\|}}{C}-R$ (R is H or alkyl) |
| β-diketone | $-\overset{\overset{O}{\|\|}}{C}-\overset{\|}{C}-\overset{\overset{O}{\|\|}}{C}-R$ (R is H or alkyl) |
| aldehyde precursor oxidizable glycol | $-\overset{\overset{OH}{\|}}{CH}-\overset{\overset{OH}{\|}}{CH_2}$ |
| hydrazine | $-NHNH_2$ |
| hydrazide | $-\overset{\overset{O}{\|\|}}{C}-NHNH_2$ |
| thiol | $-SH$ |
| amine | $-NH_2$ |
| oxyamine | $-O-NH_2$ |

[1]Exemplary carbodiimides are dicyclohexylcarbodiimide, (1-ethyl-3-(3-dimethylaminopropyl)carbodiimide, and 1-cyclohexyl-3-(2-morpholinyl)-4-ethyl carbodiimide-metho-p-toluene sulfonate.

These same reactive, functional groups can be established at the reducing end of the chitin cross-linker by reactions at the aldehyde group attached to the tetrahydrofuran ring. For example, the aldehyde group can be reacted with 1,8-diaminooctane in the presence of sodium cyanoborohydride to establish a free amino group at the reducing end of the chitin cross-linker. In turn, this free amino group can be reacted with acylating or electrophilic reagents that, in turn, lead to the presence of an alkylating, acylating, nucleophilic or electrophilic reactive functional end group on the end of the chitin cross-linker.

The functional end and side groups on the chitin cross-linker are different and compatible. This means that they do not react (or, at most, very slowly) with each other. The general literature on heterobifunctional cross-linking reagents provides many examples of functional groups that are compatible. For example, a maleimide electrophilic group and a N-hydroxysuccinimide acylating group are compatible and thereby found together on some heterobifunctional cross-linking reagents. An example is N-succinimidyl-4-(p-maleimidophenyl)butyrate (SMPB) described in Wong, S. S., "Chemistry of Protein Conjugation and Cross-Linking" CRC Press, Boca Raton, (1991), p. 153, hereby included by reference.

The chitin cross-linker can also be prepared with reactive functional groups exclusively or predominantly at its two ends instead of just at one end and along the side. This embodiment is synthesized by taking advantage of the unique chemical structure at the nonreducing end of the molecule. It is helpful, for this purpose, that the chitin cross-linker can be prepared in forms which are soluble in organic solvents like dimethylformamide. This broadens the variety of reaction conditions which can be used to place a reactive, functional group at the nonreducing end of the molecule.

The chitin cross-linker will be especially appropriate for linking biological macromolecules like different proteins, different nucleic acids, or proteins and nucleic acids together, or to solid surfaces. It will also be especially appropriate for cross-linking to and among larger biological structures such as cells. This is because these kinds of substances are large, labile, and often need to be first localized in one place, then released to go elsewhere for purification, detection, therapeutic or other purposes. This creates a need for cross-linking reagents which are very long to overcome steric effects, which have high water solubility, and which can be prepared in forms which are easily released by extremely mild, specific, biocompatible conditions. The chitin cross-linker provides these properties.

Other features and advantages of the invention will be apparent from the following description of the preferred embodiments thereof and from the claims.

EXAMPLE 1

To demonstrate the ability of the chitin cross-linker (CL-1) to function as a reversible cross-linking reagent between two different substrate proteins, it was used to link ribonuclease A to staphylococcal nuclease. First the chitin cross-linker, via its aldehyde group, was attached to ribonuclease A, at a molar ratio of 1:1.4, by incubation in the presence of sodium cyanoborohydride. Purification of the chitin cross-linker-ribonuclease A conjugate was achieved by size exclusion chromatography. The specific activity in the peak fraction for ribonuclease A was 78%.

For linkage to staphylococcal nuclease, this target enzyme was first converted to a sulfhydryl derivative by reaction with N-succinimidyl-3-(2-pyridyldithio)-propionate (SPDP) and then 2-mercaptoethanol. Based on UV measurement of the 2-thiopyridine released, the sulfhydryl derivative of the nuclease contained 1.0 sulfhydryl group per molecule. The enzymatic activity of the sulfhydryl-staphylococcal nuclease, using DNA as a substrate, was 75% relative to that of the free enzyme.

Reaction of the sulfhydryl-nuclease with the chitin cross-linker-ribonuclease A complex in a molar ratio of 1.6:1, gave the product staphylococcalnuclease-chitin cross-linker-ribonuclease A. This conjugate was purified by size exclusion chromatography. The molar ratio of the two enzymes, staphylococcal nuclease to ribonuclease A, in this conjugate was 1.0:0.94, and the yield of the conjugate was 45% from the starting chitin cross-linker-ribonuclease A complex, the limiting reagent. The two enzyme moieties in this conjugate retained, on average, 75 and 78% respectively of their activities relative to that of their native forms.

EXAMPLE 2

In a second preparation of an enzyme$_1$-chitin cross-linker-enzyme$_2$ conjugate, [$^{14}$C]acetic anhydride was used in the cross-linker synthesis reaction at the appropriate steps. The time for the coupling of the [$^{14}$C]cross-linker to ribonuclease A was increased from 42 hours to 90 hours, and the resulting molar stoichiometry of the nuclease-[$^{14}$C]chitin cross-linker-ribonuclease A in the new conjugate was 1.0:1.8:0.95. Thus, the increased time allowed for the coupling of [$^{14}$C]chitin cross-linker to ribonuclease A led to the attachment of nearly two cross-linker chains, on the average, to the enzyme. The activities of the staphylococcal nuclease and ribonuclease A moieties in this radiolabeled conjugate were 82 and 20%, respectively.

EXAMPLE 3

In order to optimize the conditions for enzymatic hydrolysis of the chitin cross-linker chain, the activity of lysozyme was compared with that of diaminooctyl-succinyl-lysozyme (DAO-succinyl-lysozyme). The latter conjugate was prepared by exhaustively reacting lysozyme with succinic anhydride, followed by coupling with 1,8-diaminooctane in the presence of a water soluble carbodiimide. An average of 1.0 DAO chains was attached to each succinyl-lysozyme molecule. The lysozyme moiety in the DAO-succinyl-lysozyme conjugate retained 99% activity on a chitin substrate relative to the use of native lysozyme at pH 7.0.

Since DAO-succinyl-lysozyme is more acidic than lysozyme, it was expected that, of the two, the first enzyme should provide a faster rate of hydrolysis of the basic two substrate-cross-linker conjugate. The hydrolysis of staphylococcal nuclease-[$^{14}$C]chitin cross-linker-ribonuclease A by lysozyme and DAO-succinyl-lysozyme was monitored by size exclusion chromatography. Based on the decreasing intensity with time of the peak for the conjugate, along with the accompanying appearance of a later-eluting, major peak for the hydrolysis products, the hydrolysis rate, as anticipated, was faster with DAO-succinyl-lysozyme than with lysozyme. For example, about 70% of the conjugate was hydrolyzed with DAO-succinyl-lysozyme after 3 hours in comparison with about 20% by lysozyme under the same conditions.

DAO-succinyl-lysozyme was, therefore, utilized for exhaustive hydrolysis of staphylococcal nuclease-[$^{14}$C]chitin cross-linker-ribonuclease A. Size exclusion chromatography showed that about 80% of the conjugate was hydrolyzed when the reaction reached equilibrium (42 hours, 37° C.). Fractions were collected, and protein concentrations and enzymatic activities were measured for each enzyme. The released staphylococcal nuclease and ribonuclease A products were 79% and 24% active relative to the native forms of these enzymes. These values are essentially the same as in the parent, radiolabeled conjugate.

Experimental Procedures

Reagents and Supplies

The cross-linking reagents, N-succinimidyl-3-(2-pyridyldithio)propionate (SPDP), bromoacetyl-N-hydroxysuccinimide ester (bromoacetyl-NHS), 5,5'-dithio-bis-(2-nitrobenzoic acid) (Ellman's reagent), 1-ethyl-3-(3-dimethylaminopropyl)carbodiimide hydrochloride (EDC), 2,4,6-trinitrobenenesulfonic acid (TNBS), 3-methyl-2-benzothiazolone hydrazone hydrochloride (MBTH), N-ethylmaleimide (NEM), glycolchitosan, egg-white lysozyme, ribonuclease A, acetic anhydride, N,N-dimethylformamide (DMF), succinic anhydride, dextrans (9.4K, 19.5K and 40.2K), 1,8-diaminooctane (DAO), and Tris(hydroxymethyl) aminomethane (Trisma base) were obtained from Sigma Chemical Co. (St. Louis, Mo.). [$^{14}$C]Acetic anhydride (50 μCi, 185 mg) was purchased from Dupont NEN Research Products (Boston, Mass.). Aminohexyl-Sepharose 4B gel and PD-10 desalting columns were obtained from Pharmacia (Piscataway, N.J.). BCA protein assay reagent was purchased from Pierce Chemical Co. (Rockford, Ill.). Centricon 10 and 30 concentrators were purchased from Amicon (Danvers, Mass.). Staphylococcal nuclease was prepared and purified as described (Shortle, J. Cell. Biochem. 30:281–289 (1986)). All other chemicals were reagent or HPLC grade unless indicated otherwise.

Equipment

High performance liquid chromatography (HPLC) was carried out with a FPLC system (Pharmacia) using a Superose 12 column from Pharmacia and a Refracto IV refractive index detector from Milton Roy (Storrs, Conn.).

Absorbance measurements including kinetic assays of enzyme activity were performed on a Lambda 3B UV/VIS spectrophotometer connected to a 3600 Data Station computer (Perkin Elmer, Wellesley, Mass.). Sample and culture incubations were done in a Model 50 shaking water bath from Precision Scientific (Chicago, Ill.), and centrifugations were performed using a Microfuge B microcentrifuge from Beckman Instruments (Carlsbad, Calif.), and an IEC Model CRU-5000 centrifuge from Fisher Chemical Co. (Medford, Mass.).

Preparation of chitin cross-linker (CL-1)

To 15 ml of 5% acetic acid containing 0.5 g of glycolchitosan, 18.75 mg of sodium nitrite (0.125 mole per mole of sugar monomer) in 0.2 ml water was added. The solution was stirred at rt for 15 min, and this step was repeated. The solution was adjusted to pH 7–8 with 10N NaOH, and 105 μl (0.5 molar excess) of acetic anhydride was added. One ml of the stirred solution was removed 15 min later for amino group measurement (see below). One hundred thirty-two mg (0.25 molar excess) of bromoacetyl NHS in 400 μl DMF was then added to the remaining sample, and another 1.0 ml of the solution was removed after 20 min. Additional acetic anhydride (840 μl) was added followed by stirring for 15 min. During the bromoacetylation and acetylation reactions, the pH was kept at 7–8 with 10N NaOH. The product was eluted with water and collected in fractions as the eluted volume 90 to 180 ml from a 5.6×15 cm P-6 column. It was then lyophilized, redissolved in 5 ml of water, and fractionated on a P-60 column (1.6×100 cm; calibrated with dextrans from Sigma) in 25 mM HEPES, 25 mM NaCl, 0.01% NAN$_3$, pH 7.0 with refraction index detection. Product fractions (50 to 60 ml) having an average estimated M$_r$ of 10,000 were pooled and dialyzed against running water (distilled and deionized) for 24 h. Lyophilization gave 65 mg of a white, cotton-like solid (CL-1) which was stored at rt in a vacuum desiccator.

Each of the above two 1.0 ml aliquots were transferred to a separate 5 ml reaction vial containing 20 mg of NaBH$_4$. After stirring at rt overnight and then extensive dialysis against water, the samples were lyophilized and stored in a vacuum desiccator until their primary amine groups were measured (see below).

Preparation of [$^{14}$C]chitin cross-linker

This product was prepared following the above procedure in a 4-fold larger scale, except that before bromoacetylation with bromoacetyl-NHS, 185 mg of [$^{14}$C]acetic anhydride (50 μCi; 1.85 MB), instead of acetic anhydride, was added to the solution.

MBTH assay

Nitrous acid oxidation followed by reaction with 3-methyl-2-benzothiazolone hydrazone hydrochloride (MBTH) and then FeCl$_3$ was used to measure the number of free amino groups (equivalent to the number of glucosamines) in the glycolchitosan and derived products (Davies et al., Meth. Enzymol. 161:442–446 (1988)). The assay was standardized with glucosamine on a weight basis. Also the MBTH/$Fe^{3+}$ stage of this procedure was used to measure the number of aldehyde groups, similarly relying on standardization with glucosamine treated with nitrous acid.

Determination of enzyme activity

Known methods were used to measure the activity of lysozyme Yamada et al., Carbohydrate Res. 92:160–162 (1981); glycolchitin substrate) and staphylococcal nuclease (Cuatrecasas et al., J. Biol. Chem. 242:1541–1547 (1967); hyperchromic shift). To measure ribonuclease A activity, 50 $\mu$l of ribonuclease A standard solutions (0, 2, 4, 6, 8 and 10 ng/ml) in 0.05% BSA, 0.5M Tris HCl, 5 mM EDTA, pH 7.5, or sample, diluted with the buffer as necessary, was added to 0.1 ml of a RNA solution (7 mg/ml highly polymerized yeast RNA in water; Calbiochem, San Diego, Calif.) in a 12×75 mm V-shaped plastic test tube. After incubation at 37° C. for 20 min, the solution was combined with 50 $\mu$l of an ice-cold 14 mmol/L solution of lanthanum acetate in 24% perchloric acid, placed in an ice bath for 5 min, and centrifuged at 1,700×g for 15 min at 4° C. A 0.1 ml aliquot of the supernatant was diluted with 1.0 ml of water for an absorbance reading at 260 nm of the acid soluble RNA.

Preparation of staphylococcal nuclease-chitin cross-linker-ribonuclease A conjugate Chitin cross-linker (10 mg, $M_r$=10K) was dissolved in 0.2 ml of 0.1M sodium acetate, pH 5.5 and combined with 0.2 ml of ribonuclease A solution (77.8 mg/ml, $E^{0.1\%}$=0.72; Cohen et al., Anal. Biochem. 144:275–284 (1985) prepared with the same buffer. $NaCNBH_3$ (0.62 mg in 20 $\mu$l of water) was added to reach a final concentration of 25 mM. After stirring at rt for 42 h, the sample was purified over a P-60 column (1.0×30 cm) in 50 mM Tris.HCl, 0.15M NaCl, pH 7.0 at 6.4 ml/h. Protein concentration in each fraction (0.64 ml) was quantified by the BCA assay. Fraction #20 was analyzed for ribonuclease A activity. Fractions 15 to 22 were pooled and centrifuge-concentrated with a Centricon 10 concentrator to give the product in a volume of 230 $\mu$l, having a protein concentration of 10.38 mg/ml.

The preparation of a control for ribonuclease A-chitin cross-linker was derived from 5 mg of the chitin cross-linker, 3.75 mg of glycine (100 fold excess over the chitin cross-linker), and 0.314 mg of $NaCNBH_3$ in a total volume of 110 $\mu$l. The solution was stirred at rt for 18 hr prior to the addition of 0.1 ml of the ribonuclease A solution (77.8 mg/ml) and was stirred for an additional 30 h. The purification and assay procedures were followed as above.

Staphylococcal nuclease (7.67 mg in 0.3 ml of 0.1M sodium phosphate, 0.15M NaCl, pH 7.5) was treated with 0.287 mg (2-fold molar excess over staphylococcal nuclease) of SPDP in 0.1 ml of DMF for 2.5 h at rt. To generate sulfhydryl staphylococcal nuclease, 1 $\mu$l of 2-mercaptoethanol was added. The resulting sample was centrifuge-purified on a PD-10 column, and 0.3 ml was combined with 160 $\mu$l of chitin cross-linker-ribonuclease A, bubbled with $N_2$ for 2 min, and stirred at rt for 48 h in the dark. The purification of the resulting staphylococcal nuclease-chitin cross-linker-ribonuclease A conjugate was carried out on a P-100 column (1.0×30 cm) in 50 mM sodium phosphate, 0.15M NaCl, pH 7.0 at a flow rate of 6.2 ml/h. Fractions 8 to 15 ml were pooled for rechromatography under the same conditions. Protein quantitation by BCA, enzyme-activity assays and disulfide content determinations were performed on each elution fraction (0.67 ml). Ellman's reagent was used for the latter measurement (Habeeb, A.F.S.A., Meth. Enzymol. XXV:457–464 (1972)).

A control for the preparation of staphylococcal nuclease-chitin cross-linker-ribonuclease A conjugate was derived from 0.1 ml of sulfhydryl staphylococcal nuclease that was quenched with 144 $\mu$g (30-fold molar excess over the sulfhydryl staphylococcal nuclease) of NEM in 12 $\mu$l of DMF for 10 min at rt, followed by the addition of 50 $\mu$l of the chitin cross-linker-ribonuclease A solution. The sample was subjected to the same reaction and purification procedures.

Preparation of [$^{14}$C]conjugate

The above procedure was followed with the following exceptions: (1) The scale was a 4-fold larger; (2) 50 mM of $NaCNBH_3$, 0.1% $NaN_3$ and a 90 h incubation were used to prepare [$^{14}$C]chitin cross-linker-ribonuclease A; and (3) the reaction period for the preparation of staphylococcal nuclease-[$^{14}$C]chitin cross-linker-ribonuclease A was 96 h. The purified staphylococcal nuclease-[$^{14}$C]chitin cross-linker-ribonuclease A (1.89 mg/ml) was stored at −20° C. in aliquots.

Preparation of DAO-succinyl-lysozyme

A 70 ml volume of 0.2M sodium phosphate, pH 7.4 containing 800 mg of lysozyme (determined by an absorbance measurement at 281.5 nm, $E^{0.1\%}$=2.64; (Aune et al., Biochem. 8:4579–4585 (1969)) was combined with 278 mg (50-fold molar excess) of succinic anhydride and stirred at rt for 30 min, followed by 278 mg more succinic anhydride. After 2.5 h, the lysozyme was dialyzed overnight against running distilled water, filtered through a paper filter (size 4, Whatman, England) on a glass funnel and lyophilized. The product was stored at −20° C.

Succinyl-lysozyme (413 mg) was dissolved in 15 ml of 1M DAO. After the pH was adjusted to 5.0 with 1N HCl, 11 mg (2-fold molar excess over succinyl-lysozyme) of EDC was added. After stirring at rt for 80 min, the solution was dialyzed for 48 h against running distilled water. To redissolve most of the precipitate formed during the dialysis, 0.4 ml of 4M $K_2HPO_4$ was added to the dialysate, giving pH~8.0, followed by filtration and lyophilization. The product was stored at −20° C.

Hydrolysis of staphylococcal nuclease-[$^{14}$C]chitin cross-linker-ribonuclease A Staphylococcal nuclease-[$^{14}$C]chitin cross-linker-ribonuclease A (0.2 ml, 1.89 mg/ml) was treated with 50 $\mu$g of lysozyme or DAO-succinyl lysozyme in 50 $\mu$l of 50 mM sodium phosphate, 0.1M NaCl, 1 mM EDTA, pH 7.0 in a 12×75 mm plastic test tube. After incubation at 37° C., 10 $\mu$l aliquots were injected into a Superose 12 column as a function of time (mobile phase: 0.1M HEPES, 0.5M NaCl, 1 mM EDTA, pH 7.2 at 0.6 ml/min) with monitoring by UV (280 nm). Fractions were collected and analyzed for protein concentration (BCA assay) and also ribonuclease A and staphylococcal nuclease activities.

EXAMPLE 4

A number of other embodiments of a chitin cross-linker can be prepared, having the functional side and end groups as indicated.

(CL-2) Bromoacetyl(side)/Carboxyl(end) Chitin Linker

The chitin cross-linker prepared as described above (CL-1) is reacted with 6-aminohexanoic acid in the presence of NaCNBH$_3$ to afford CL-2. CL-2 can be activated with a carbodiimide reagent.

(CL-3) Bromoacetyl(side)/Amino(end) Chitin Linker

CL-1 is reacted with 1,8-diaminooctane in the presence of NaCNBH$_3$ to afford CL-3.

(CL-4) Bromoacetyl(side)/Hydrazide(end) Chitin Linker

CL-1 is reacted with adipic acid dihydrazide in the presence or absence of NaCNBH$_3$ to afford CL-4.

(CL-5) Bromoacetyl(side)/Carboxyl(end) Chitin Linker

CL-3 is reacted with succinic anhydride to afford CL-5.

(CL-6) Maleimide(side)/Aldehyde(end) Chitin Linker

Glycolchitosan-CHO is reacted with acetic anhydride and a maleimide-NHS reagent (e.g., SMCC (succinimidyl 4-(N-maleimidomethyl)cyclohexane-1-carboxylate); Sulfo-SMCC (sulfosuccinimidyl 4-(N-maleimidomethyl)cyclohexane-1-carboxylate); MBS (m-maleimidobenzoyl-N-hydroxysuccinimideester); Sulfo-MBS (m-maleimidobenzoyl-N-hydroxysulfosuccinimide ester); SMPB (succinimidyl 4-(p-maleimidophenyl)butyrate; or Sulfo-SMPB (sulfosuccinimdyl 4-(p-maleimido-phenyl)butyrate; from Pierce Chemical Co. to afford CL-6.

(CL-7) Bromoacetyl(side)/Azidophenyl(end) Chitin Linker

CL-1 is reacted with azidobenzoyl hydrazide (ABH; Pierce) in the presence or absence of NaCNBH$_3$ to afford CL-7. The azide moiety can be activated to a reactive nitrene by photolysis.

(CL-8) Bromoacetyl(side)/Aldehyde(end) Chitin Linker

Cyanoethyl (CE)-, carboxymethyl (CM)-, or propyleneglycol (PG)-chitosan is reacted in the same way as glycol chitosan with nitrous acid, acetic anhydride and bromoacetyl-NHS to afford CE-, CM-, or PG-CL-8.

(CL-9) Amino(side)/Disulfide(end) Chitin Linker

Glycolchitosan-CHO is reacted with acetic anhydride and succinic anhydride, ethylenediamine/NaCNBH$_3$, SPDP, and 1,8-diaminooctane/carbodiimide to afford CL-9.

(CL-10) Amino(side)/Thiol (end) Chitin Linker

Cl-9 is reacted with dithiothreitol to afford CL-10.

(CL-11) Bromoacetyl(side)/NHS Ester(end) Chitin Linker

CL-3 is reacted with disuccinimidyl suberate (Pierce) to afford CL-11, or CL-5 is reacted with a carbodiimide and N-hydroxysuccinimide to afford CL-11.

(CL-12) Carboxyl(side)/Hydrazide(end) Chitin Linker

Glycolchitosan-CHO is reacted with acetic anhydride and succinic acid (or with just succinic anhydride), and then with adipic acid dihydrazide/NaCNBH$_3$, to afford CL-12.

(CL-13) Bromoacetyl(side)/Aldehyde(end) Chitin Linker

Glycolchitosan-CHO is reacted with propionic anhydride or benzoic anhydride, and with bromoacetyl-NHS, to afford CL-13.

(CL-14) Bromoacetyl(side)/Oxidizable Glycol(end) Chitin Linker

CL-3 is reacted with epibromohydrin (Aldrich) and then aqueous acid to afford CL-14. The oxidizable glycol can be converted to a reactive aldehyde group with aqueous sodium periodate.

(CL-15) Maleimide(end)/Aldehyde(end) Chitin Linker

Cyanoethylchitosan is reacted with HONO and acetic anhydride, followed by reaction with 4-maleimidobenzoyl chloride (Wong Book p. 161) to afford CL-15.

(CL-16) Oxidizable Glycol(end)/Carboxyl(end) Chitin Linker

Cyanoethylchitosan is reacted with nitrous acid and acetic anhydride, followed by reaction with adipic acid dihydrazide/NaCNBH$_3$, succinic anhydride, epibromohydrin, and aqueous acid to afford CL-16. The oxidizable glycol can be activated to a reactive aldehyde group by aqueous sodium periodate.

(CL-17) Maleimide(end)/Amino(end) Chitin Linker

CL-15 is reacted with 1,8-diaminooctane/NaCNBH$_3$ to afford CL-17.

(CL-18) Oxidizable Glycol(end)/Hydrazide(end) Chitin Linker

CL-16 is reacted with adipic acid dihydrazide/carbodiimide to afford CL-18.

(CL-19) Oxidizable Glycol(end)/Thiol(end) Chitin Linker

CL-18 is reacted with 2-iminothiolane to afford CL-18.

(CL-20) Amino (end)/Carboxyl (end) Chitin Linker

CL-15 is reacted with 2-mercaptoethylamine to afford CL-20.

(CL-21) Amino(end)/Maleimide(end) Chitin Linker

Cyanoethylchitosan is reacted with HONO and then acetic anhydride, followed by reaction with ethylenediamine/NaCNBH$_3$, a maleimide-NHS reagent (see CL-6), carbonyldiimidazole and 1,8-diaminooctane to afford CL-21.

(CL-22) Epoxy(end)/Carboxyl(end) Chitin Linker

Cyanoethylchitosan is reacted with HONO and then acetic anhydride, 6-aminohexanoic acid/NaCNBH$_3$, and 1,4-bis(2,3-epoxypropoxy)butane to afford CL-22. Alternatively, epichlorohydrin may be used in place of 1,4-bis(2,3-epoxypropoxy)butane.

(CL-23) Maleimide(end)/Carboxyl(end) Chitin Linker

Glycolchitosan-CHO or cyanoethylchitosan-CHO is reacted with acetic anhydride, adipic acid dihydrazide/NaCNBH$_3$, succinic anhydride, and benzaldehyde/ZnCl$_2$ or benzaldehyde/HCl (or cyclohexanone dimethylketal/p-toluenesulfonic acid or 2,2-dimethoxypropane p-toluenesulfonic acid), giving benzylidene CL-23 (Bzd-CL-23). The latter is reacted with acetic anhydride/pyridine, palladium/H$_2$ (or aqueous acid), and 4-maleimidobenzoyl chloride to afford CL-23.

(CL-24) Amino(end)/Carboxyl(end) Chitin Linker

Bzd-CL-23 is reacted with acetic anhydride/pyridine, palladium/H$_2$, cyanogen bromide, and 1,6-hexanediamine to afford CL-24.

(CL-25) Maleimide(end)/Carboxyl(end) Chitin Linker

Glycolchitosan-CHO or cyanoethylchitosan-CHO is reacted with acetic anhydride, 6-aminohexanoic acid methyl ester/NaCNBH$_3$, benzaldehyde/ZnCl$_2$ or benzaldehyde/HCl (or cyclohexanone dimethylketal/p-toluenesulfonic acid or 2,2-dimethoxypropane/p-toluenesulfonic acid), acetic anhydride/pyridine, palladium/H$_2$ (or aqueous acid), cyanogen bromide, 1,6-hexanediamine, aqueous sodium hydroxide, and a maleimide-NHS reagent (see CL-6) to afford CL-25.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A carbohydrate cross-linking reagent comprising a sequence of substituted glucosamine units in β-1,4 linkage, said sequence having at the reducing end a tetrahydrofuran unit, said reagent having the formula

[structural formula]

wherein

R$_1$, R$_2$ is H, (CH$_2$CH$_2$O)$_m$H, (CH$_2$CH[CH$_3$]O)$_m$H, CH$_2$CO$_2$H, or CH$_2$CH$_2$CN, wherein m is an integer in the range of 1–10;

n is greater than or equal to 2;

R$_3$ and R$_4$ are acylating, alkylating, electrophilic or nucleophilic reactive substituents which are different from each other but mutually compatible neither R$_3$ nor R$_4$ is an acyl group, and at least one R$_4$ is present; and R$_5$ is an acyl group.

2. A carbohydrate cross-linking reagent comprising a sequence of substituted glucosamine units in β-1,4 linkage, said sequence having at the reducing end a tetrahydrofuran unit, said reagent having the formula

[structural formula]

wherein

R$_1$, R$_2$ is H, (CH$_2$CH$_2$O)$_m$H, (CH$_2$CH[CH$_3$]O)$_m$H, CH$_2$CO$_2$H, or CH$_2$CH$_2$CN, wherein m is an integer in the range of 1–10;

n is greater than or equal to 1;

R$_3$ and R$_4$ are acylating, alkylating, electrophilic or nucleophilic reactive substituents which are different from each other but mutually compatible neither R$_3$ nor R$_4$ is an acyl group; and R$_5$ is an acyl group.

3. The cross-linking reagent of claim 1 or claim 2 wherein n is greater than or equal to 10.

4. The cross-linking reagent of claim 1 or claim 2 wherein n is in the range of 10–100.

5. The cross-linking reagent of claim 1 or claim 2 wherein R$_1$ is (CH$_2$CH$_2$O)$_m$H.

6. The cross-linking reagent of claim 1 or claim 2 wherein R$_1$, is (CH$_2$CH[CH$_3$]O)$_m$H.

7. The cross-linking reagent of claim 1 or claim 2 wherein R$_1$ is CH$_2$CO$_2$H.

8. The cross-linking reagent of claim 1 or claim 2 wherein R$_1$ is CH$_2$CH$_2$CN.

9. The cross-linking reagent of claim 1 or claim 2 wherein R$_1$ H.

10. The cross-linking reagent of claim 1 or claim 2 wherein R$_2$ is H.

11. The cross-linking reagent of claim 1 or claim 2 wherein R$_3$ or R$_4$ is an acylating reactive substituent.

12. The cross-linking reagent of claim 1 or claim 2 wherein R$_3$ or R$_4$ is an alkylating reactive substituent.

13. The cross-linking reagent of claim 1 or claim 2 wherein R$_3$ or R$_4$ is an electrophilic reactive substituent.

14. The cross-linking reagent of claim 1 or claim 2 wherein R$_3$ or R$_4$ is an nucleophilic reactive substituent.

15. The cross-linking reagent of claim 1 or claim 2 wherein R$_5$ is acetyl.

16. The cross-linking reagent of claim 1 or claim 2 wherein R$_5$ is propionyl or benzoyl.

17. The cross-linking reagent of claim 1 wherein n is about 40; R$_2$ is H; R$_3$ is CHO; R$_4$ is COCH$_2$Br; and R$_5$ is COCH$_3$.

* * * * *

UNITED STATES PATENT AND TRADEMARK OFFICE
CERTIFICATE OF CORRECTION

PATENT NO. : 5,412,083
DATED : May 2, 1995
INVENTOR(S) : Roger W. Giese, et al

It is certified that error appears in the above-indentified patent and that said Letters Patent is hereby corrected as shown below:

Column 2, in the formula located between lines 41 and 54, the bracket is missing over $R_4$, $R_5$.

Column 2, line 56, "$CH_2CO_2$ or" should read --$CH_2CO_2H$, or--.

Column 8, line 39, "staphylococcalnuclease-chitin" should read --staphylococcal nuclease-chitin--.

Column 11, line 8, "lysozyme Yamada" should read --lysozyme (Yamada--.

Column 16, line 42, "wherein $R_1$ H" should read --wherein $R_1$ is H--.

Signed and Sealed this

Second Day of July, 1996

Attest:

BRUCE LEHMAN

Attesting Officer    Commissioner of Patents and Trademarks